US010102473B1

(12) United States Patent
Anderson et al.

(10) Patent No.: US 10,102,473 B1
(45) Date of Patent: Oct. 16, 2018

(54) SOIL MOISTURE SENSING DETERMINES SOIL TYPE

(71) Applicants: Scott K. Anderson, Meridian, ID (US); Hyrum S. Anderson, Eagle, ID (US)

(72) Inventors: Scott K. Anderson, Meridian, ID (US); Hyrum S. Anderson, Eagle, ID (US)

(73) Assignee: Technical Development Consultants, Inc., Meridian, ID (US)

(*) Notice: Subject to any disclaimer, the term of this patent is extended or adjusted under 35 U.S.C. 154(b) by 0 days.

(21) Appl. No.: 15/702,640

(22) Filed: Sep. 12, 2017

(51) Int. Cl.
| | | |
|---|---|---|
| *G06N 3/02* | (2006.01) | |
| *G06N 3/04* | (2006.01) | |
| *G01N 27/04* | (2006.01) | |
| *G06N 3/08* | (2006.01) | |
| *G01N 15/08* | (2006.01) | |
| *G01N 33/24* | (2006.01) | |

(52) U.S. Cl.
CPC ............ *G06N 3/04* (2013.01); *G01N 15/088* (2013.01); *G01N 27/048* (2013.01); *G01N 33/24* (2013.01); *G06N 3/02* (2013.01); *G06N 3/08* (2013.01)

(58) Field of Classification Search
CPC ....................................................... G06N 3/02
USPC ............................................................ 706/21
See application file for complete search history.

(56) References Cited

U.S. PATENT DOCUMENTS

| 6,657,443 B2 | 12/2003 | Anderson |
| 6,831,468 B2 | 12/2004 | Anderson |

OTHER PUBLICATIONS

Zou al ("Artificial neural network and time series models for predicting soil salt and water content" 2009).*

(Continued)

*Primary Examiner* — Lut Wong
(74) *Attorney, Agent, or Firm* — Your Intellectual Property Matters, LLC; Robert A. Frohwerk

(57) ABSTRACT

Digitized images of the propagated waveforms returned by Time-Domain (TD) sensors reveal the effects of bound water in soil samples, causing errors in the volumetric water content reported for samples due to soil type. Pattern analysis yields not only correct volumetric water content values but also the soil type from which the waveform was taken. Collection and analysis of waveforms from soils having precisely known properties yield computer-generated algorithms to improve the accuracy and number of reporting variables for integrated TD sensors. These algorithms can be deployed in the Cloud for external analysis, or can be incorporated within the sensor to report highly accurate readings of water content, conductivity and soil type under all conditions of these variables with no interpretive burden placed on the user of the sensor. Machine learning algorithms are intended to externally augment data measured by these sensors, or can be added to similar sensors.

15 Claims, 6 Drawing Sheets

(56) References Cited

OTHER PUBLICATIONS

Khojasteh et al ("Using of Artificial Neural Networks for Evaluation Soil Water Content with Time Domain Reflectometry" 2010).*
Taechatanasat et al ("Decision Support System Data for Farmer Decision Making" 2013).*
Biswas et al ("Application of ContinuousWavelet Transform in Examining Soil Spatial Variation: A Review" 2011).*
Dursun et al ("An efficient improved photovoltaic irrigation system with artificial neural network based modeling of soil moisture distribution—A case study in Turkey" 2014).*
Corwin et al ("Apparent soil electrical conductivity measurements in agriculture" 2005).*
Arsoy et al ("Enhancing TDR based water content measurements by ANN in sandy soils" 2013).*

\* cited by examiner

SOIL MOISTURE SENSING DETERMINES SOIL TYPE

FIELD OF THE INVENTION

The present invention relates generally to analysis of a material to determine its physical properties. In particular, the described methods pertain to sampling of soil to determine soil parameters, including volumetric water content, electrical conductivity and soil type.

BACKGROUND

A preferred method of measuring the water content of various media, including soils, is to insert a waveguide into the medium and measure the propagation time of a voltage impulse or step function through the medium. Details of such methods have been described in U.S. Pat. Nos. 6,657,443 and 6,831,468 which make use of the fact that the propagation time of an electromagnetic wave is proportional to the square root of the permittivity of the medium through which the wave travels.

It is also known that relative permittivity of water is about 80 times that of free space and typically 30 times that of the minerals found in soils. By measuring propagation time, it is then possible to accurately determine the permittivity and also the water content of the medium. Since these measurements are temporal and not based on current and voltage relationships, the resulting water content measurements are free from the effects of the electrical properties of the soil, such as electrical conductivity. There are, however, other soil properties that have an impact on temporal measurements and introduce errors in permittivity and water content measurements.

BRIEF DESCRIPTION

When an electromagnetic pulse is propagated through a medium such as soil, the resulting waveform is affected differently depending upon whether or not the water is bound to the soil particles. When a soil sample is comprised of fine particles, such as clay, soil moisture is more likely to be in the form of "bound water", whereas the larger grain size of sand reduces the proportion of water that is in close proximity to the soil particles. With the recognition that definite patterns exist, it is possible to not only derive the correct water content of a soil sample but also to determine its soil type.

BRIEF DESCRIPTION OF THE DRAWINGS

The particular features and advantages of the devices described herein will become apparent from the following description when taken in conjunction with one or more of the accompanying FIGS. 1-6 of the drawings.

Figure 1:
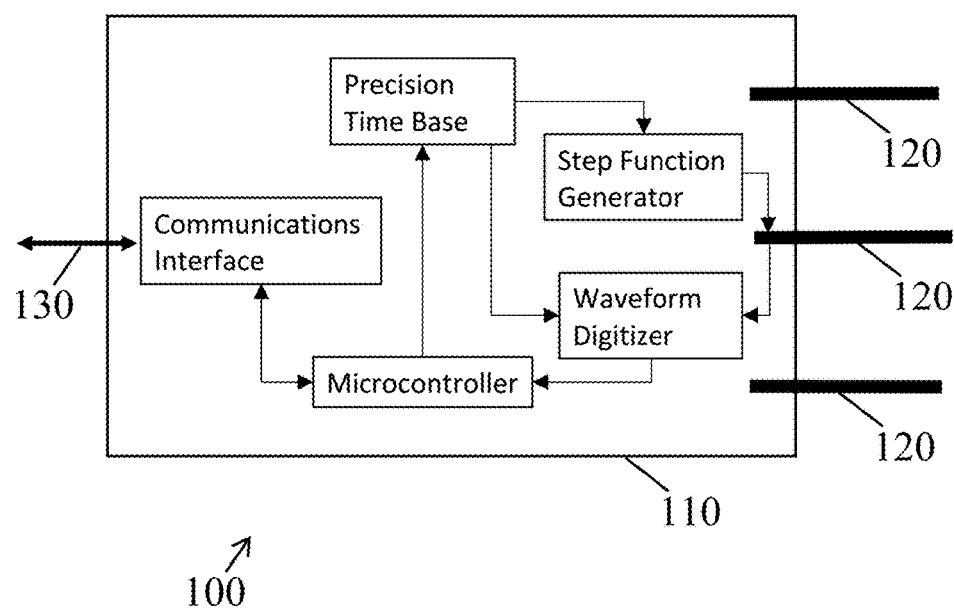
FIG. 1 is a block diagram of an Integrated Time-Domain Reflectometer (TDR) used to generate Time-Domain Waveforms.

The following Reference Numbers may be used in conjunction with one or more of the accompanying FIGS. 1-6 of the drawings:
100 Time-Domain Reflectometer (TDR) system
110 Integrated TDR module
120 waveguide
130 cable to radio or data recorder
140 radio transmitter
145 mount to support radio transmitter
150 transmission to/from TDR sensor
200 soil surface
210 Reflected Wave in clayey soil
215 marker of onset of reflected wave in clayey soil
220 Reflected Wave in silty soil
225 marker of onset of reflected wave in silty soil All references to "waveform" in this document are intended to refer to time-domain waveforms acquired by a time-domain sensor, unless otherwise specified.

DETAILED DESCRIPTION

One factor that introduces errors in permittivity and water content measurements of soil is a phenomenon in which water molecules that are in close proximity to soil particles tend to respond to an applied electrical field more slowly than those water molecules that are away from the surfaces of soil particles. Those water molecules that are impacted by this phenomenon are referred to as 'bound water'. Large particle soils such as sand and mid-range soils such as loam or silt tend to show negligible effects from bound water, but in fine soils, such as clay, the pore spaces are much smaller and the portion of the water molecules that are in close proximity to the soil particles is quite significant.

The block diagram of FIG. 1 illustrates a configuration of a time-domain waveform data generator based upon the teachings of U.S. Pat. No. 6,657,443 and U.S. Pat. No. 6,831,468. Using Time-Domain Reflectometry (TDR), successive fast transitions produced by a Step Function Generator are injected into a Waveguide 120 immersed in a medium, or material, of interest, such as soil. A Waveform Digitizer receives a characteristic waveform to be digitized. Pertinent information is collected by a data collection system under control of a Microcontroller toward construction of a profile of the material. This information may be forwarded to a Communications Interface. A cable 130 may connect the Communications Interface to a radio transmitter for broadcast to a remote location or for insertion to the Internet. Alternately, cable 130 may connect to a nearby data recorder or display.

Figure 2:
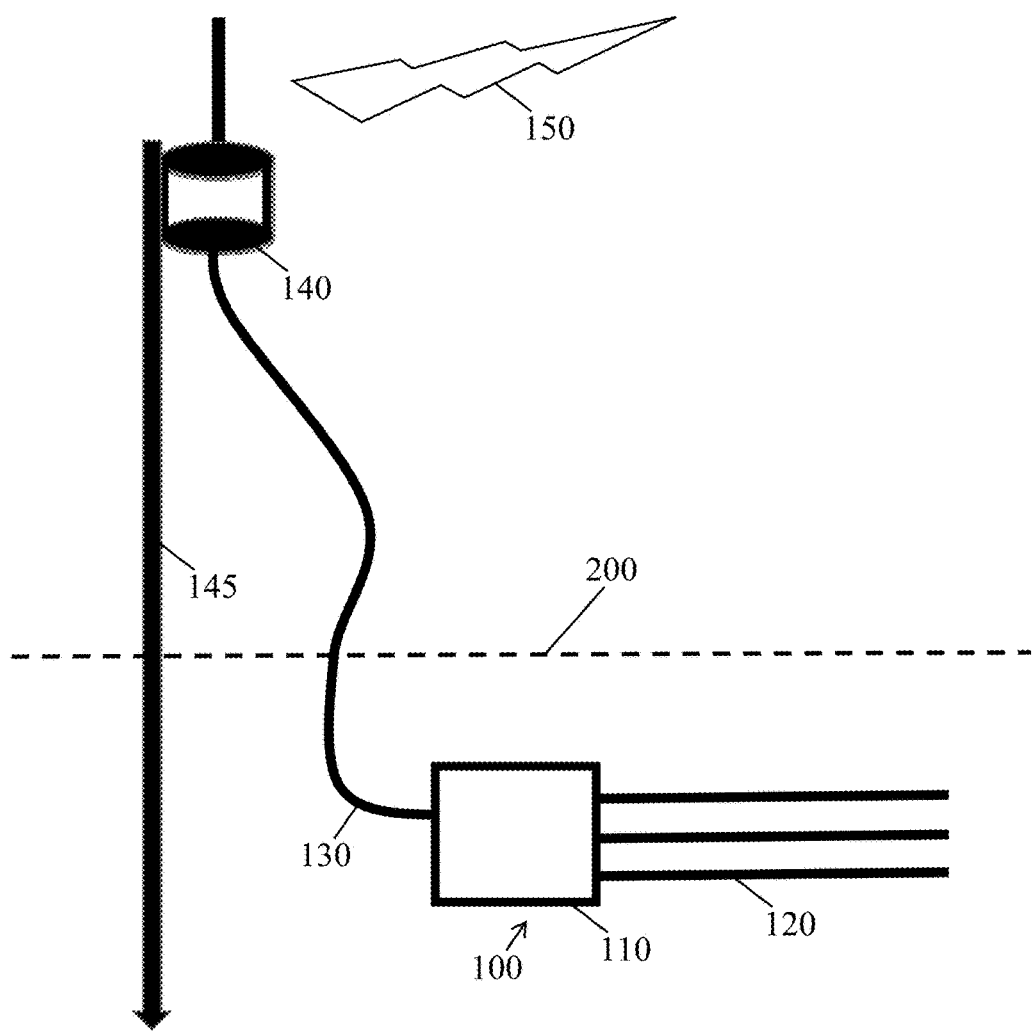
FIG. 2 depicts an Integrated TDR embedded in soil with a radio link for a remote connection.

One implementation of a system employing the Integrated Time Domain Reflectometer (TDR) of FIG. 1 is depicted in FIG. 2. Here the TDR system 100 with its Integrated TDR Module 110 and its associated waveguide 120 is embedded in the soil, buried below the soil surface 200, to sample the soil to create a soil profile. The cable 130 connects the TDR system to the world above ground. As shown, the cable is connected to a radio transmitter 140 mounted on a support 145 which is anchored into the soil. The radio transmitter 140 allows transmission 150 between the TDR sensor and a remote user, whether such user is at a nearby field-based monitor station accessible by Bluetooth or Wi-Fi, or in-the-cloud and accessible by connection to the Internet. Alternately, the radio transmitter 140 may be replaced by a local data recorder or display or other very basic readout device which may be useful for set up of a particular installation or for taking field readings with a portable, as opposed to buried, TDR system.

Figure 3:
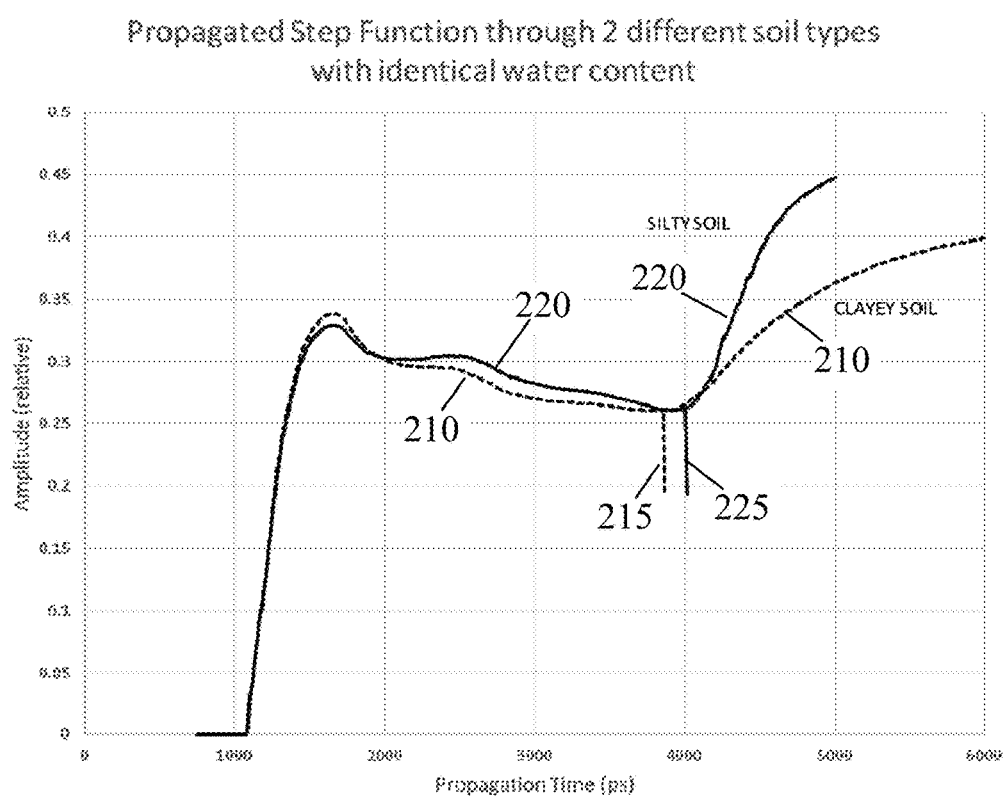
FIG. 3 shows Time-Domain Waveforms for two different soil types having the same water content.

When in operation, the waveguide 120 of the TDR sensor 100 receives waveforms such as those depicted in the plot of FIG. 3, wherein the ordinate is time in pico-seconds, and the abscissa is amplitude in volts. The effects of dispersion caused by the conductive and dielectric properties of the soil on the waveform are extrapolated by detecting the bulk propagation time and the slope of the distorted rising edge of the characteristic received waveform as described in U.S. Pat. Nos. 6,657,443 and 6,831,468. Absolute volumetric moisture percentage is inferred from propagation time, and absolute electrical conductivity of the soil is inferred from the maximum slope value of the distorted rising edge of the characteristic received waveform.

The two reflected waveforms (210, 220) of FIG. 3 are acquired from two soil samples; reflected waveform 210 is from a clayey soil with reflected waveform 220 being acquired from a silty soil. Both soil samples have the same water content and differ only in their soil types. The left side of the waveform plots begin with the incident wave generated by the step function generator within the sensor as it is applied to the incident end of the waveguide 120. As the wave propagates down the waveguide it excites all nearby polar particles, water being a polar molecule, and causes them to line up with the electric field, assuming that they are free to do so. As the polar particles line up, the electric field is enhanced by the addition of their presence.

The vertical markers (215 and 225) on the waveforms show the onset of the reflected wave. Marker 215 is associated with soil classified as "Pullman Soil" containing 40% clay. Marker 225 indicates the onset of the reflected wave in a silty soil (from the "Norfolk Soil" family) having only a 2% clay content. The balance of both samples comprises loam and fine sand. The basic difference between the soils is pore, or particle, size). The clay-bearing soil waveform 210 shows an initial response that is somewhat earlier than the expected response for the amount of water present. It also shows a sluggish rise after the initial response. The non-clay bearing soil produces a reflected waveform 220 showing an initial rise at the point where it is expected which then rises more rapidly than the clay-bearing soil waveform 210. This behavior occurs at least in part due to the water pores in the clay soil being so small that many of the water molecules are close to the surfaces of the clay particles and are somewhat attracted to those surfaces, slowing their response to the fast rising incident electric field. The molecules that are away from the clay surfaces respond quickly. Those that are bound by the clay respond sporadically at a later time, as much as 2 ns later in the depicted waveform (210).

These two plots clearly show that there is a recognizable difference in the waveform responses of soils with differing pore sizes. However, quantifying those differences is a very complex task and is rendered more complex by the electrical conductivity of soil. Electrical conductivity is sensitive to temperature and compaction, as well as to volumetric water content (VWC), the very variable being sought in the analysis. (For brevity, in this document, "water content" may be taken as being synonymous with "volumetric water content".) These complexities make it very difficult to derive mathematical models for finding water content among all the affecting variables. Fortunately, the science referred to as 'Big Data' Analysis or Data Analytics is capable of distilling the essential metrics from a complex set of variables without the use of complex mathematical models. This case of deriving soil moisture from complex waveform patterns is to be referred to as "Soil Waveform Analytics".

The pertinent analysis is conducted on thousands of sampled waveforms and their associated precisely measured water content, electrical conductivity, temperature, compaction and soil type. Special data analytics methods and computers are applied to the large data sets to uncover patterns and develop algorithms that associate key waveform characteristics to the sought after variables of water content, electrical conductivity of the soil, permittivity and soil type. Deep learning techniques are leveraged to develop empirical models of the relationships between those system inputs that are directly measured and key soil characteristics that are predicted. Measured inputs include digitized waveforms, temperature, and electrical conductivity of the soil, and the sensor geometry of the sensing rod, including its length, whereas volumetric water content (VWC) and soil type are two examples of soil characteristics that may be predicted by a deep learning system.

An additional benefit to the deep learning analysis of Time-domain waveforms is that water content can be directly derived from the waveform characteristics rather than from permittivity as is the current practice. The conversion from permittivity to water content relies upon the Topp equation or a suitable dielectric mixing model. Both of these contain significant errors for some soil types and for some ranges of water content. These errors can be eliminated by developing a direct deep learning approach to water content to improve measurement accuracy over a wide range of soil parameters.

Figure 4:
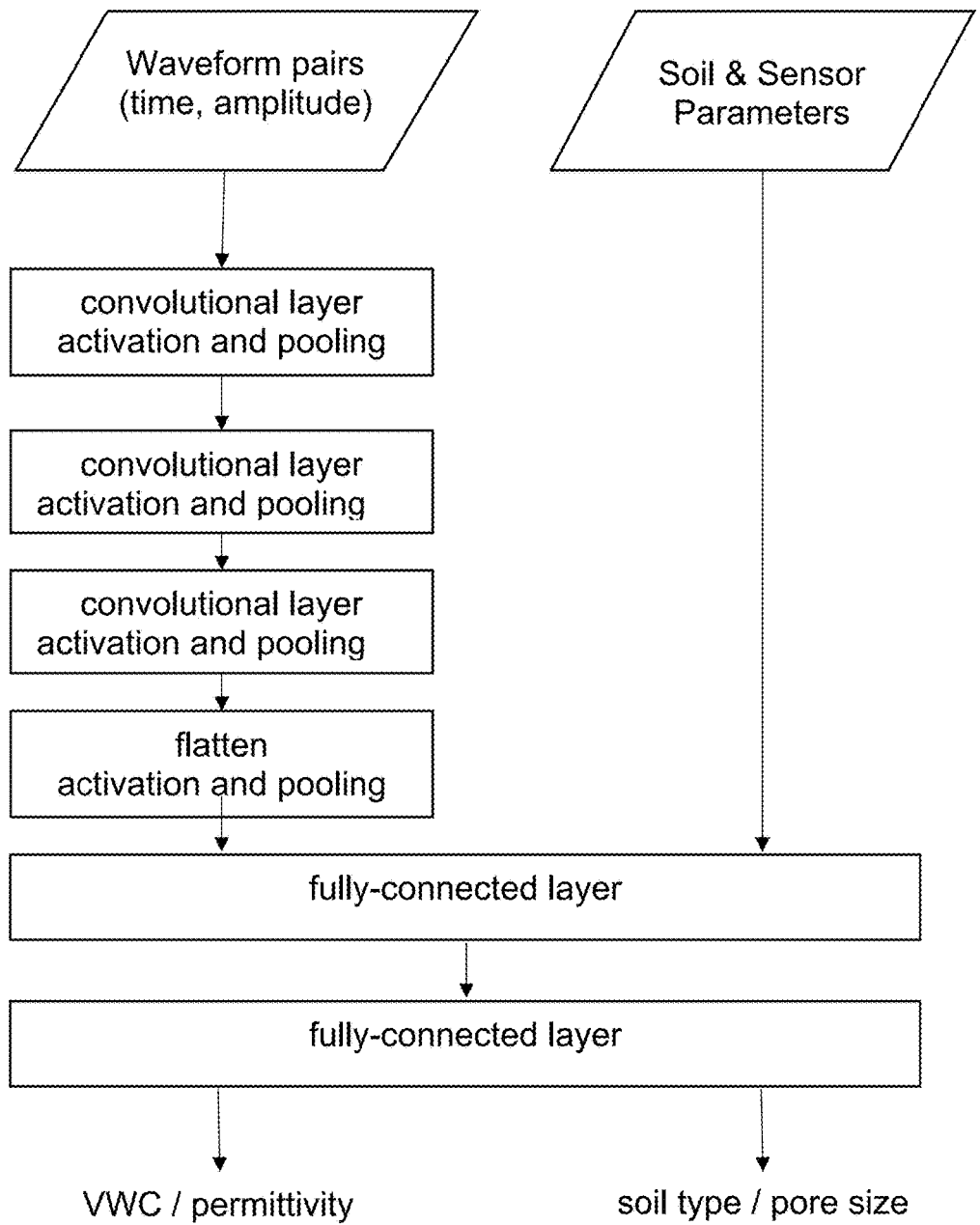
FIG. 4 outlines the components for creation of a TDR/Soil Model.

When waveforms can be collected, a computer-implemented machine learning model is selected. One approach is to use a deep neural network architecture (one form of "deep learning") as shown in FIG. 4. The network consists of several preliminary convolutional layers that operate on both the amplitude and temporal dimensions of the input waveform, and learn to recognize locally relevant features of the waveforms. The network commences with several fully-connected hidden layers that include as inputs the output of the convolutional layer, but also the directly measured parameters such as soil temperature, electrical conductivity of the soil and sensor (rod) geometry. The network concludes with an output layer that predicts volumetric water content, and a categorical predictor of the probability that a soil sample belongs to one of several soil types. An alternative embodiment to the soil category prediction is a soil pore size predictor which consists of a single real-valued output that corresponds to pore size.

Figure 5:
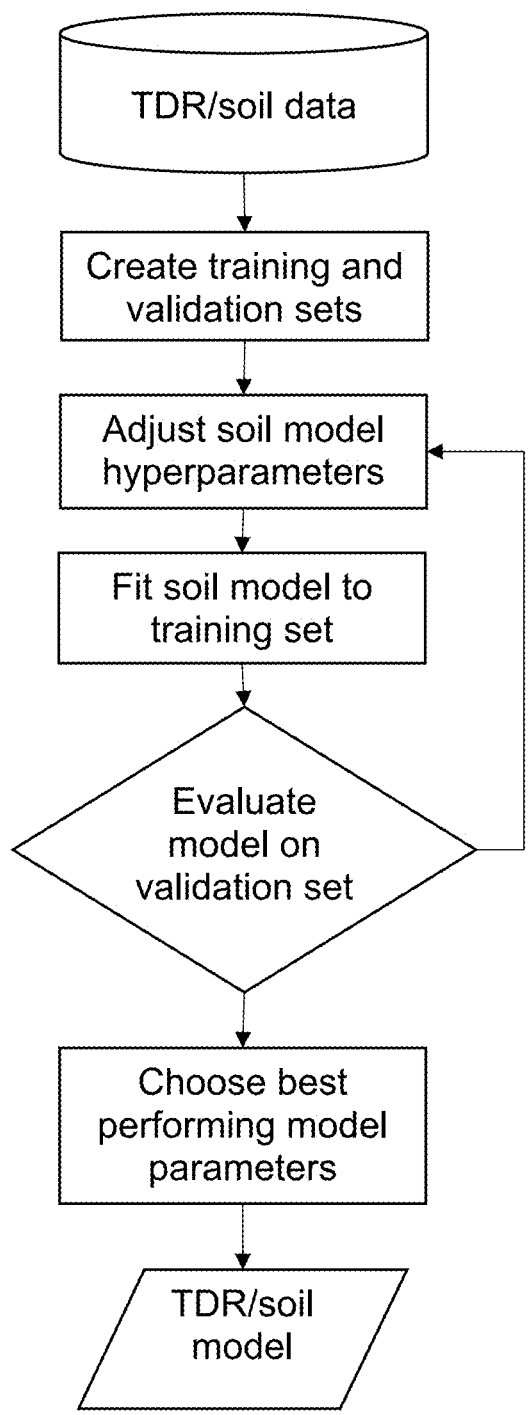
FIG. 5 flowcharts an off-line training process.

Once a model has been created, it must be trained. Training of a selected model may be done off-line as depicted in FIG. 5 beginning with collection of a large dataset consisting of thousands of digitized waveforms recorded with associated physical parameters that can be measured directly or are pre-defined. Such physical parameters include soil temperature, electrical conductivity and rod length of the Time-Domain Sensor. Each digitized waveform consists of hundreds of data points in the form of (time, amplitude) pairs. The data pairs necessarily capture the transient step response of various soils to an incident wave.

Each waveform is also associated with the desired output parameters, including volumetric water content and the corresponding soil type and pore size. The volumetric water content is commonly measured by the gravimetric method, while the soil type and pore size are established by mixing samples of soils having known parameters. Data collection and measurement of waveforms require a significant investment in time, and must be given careful attention.

As the selected model is presented with sets of data for validation, the predicted outputs are examined to evaluate the model. The hyperparameters of the soil model are adjusted in a feedback loop to improve the performance of the model. Upon achieving suitable performance of an empirical deep learning model that is trained off-line on thousands of digitized waveforms, the trained model is ready to be put into use.

Figure 6:
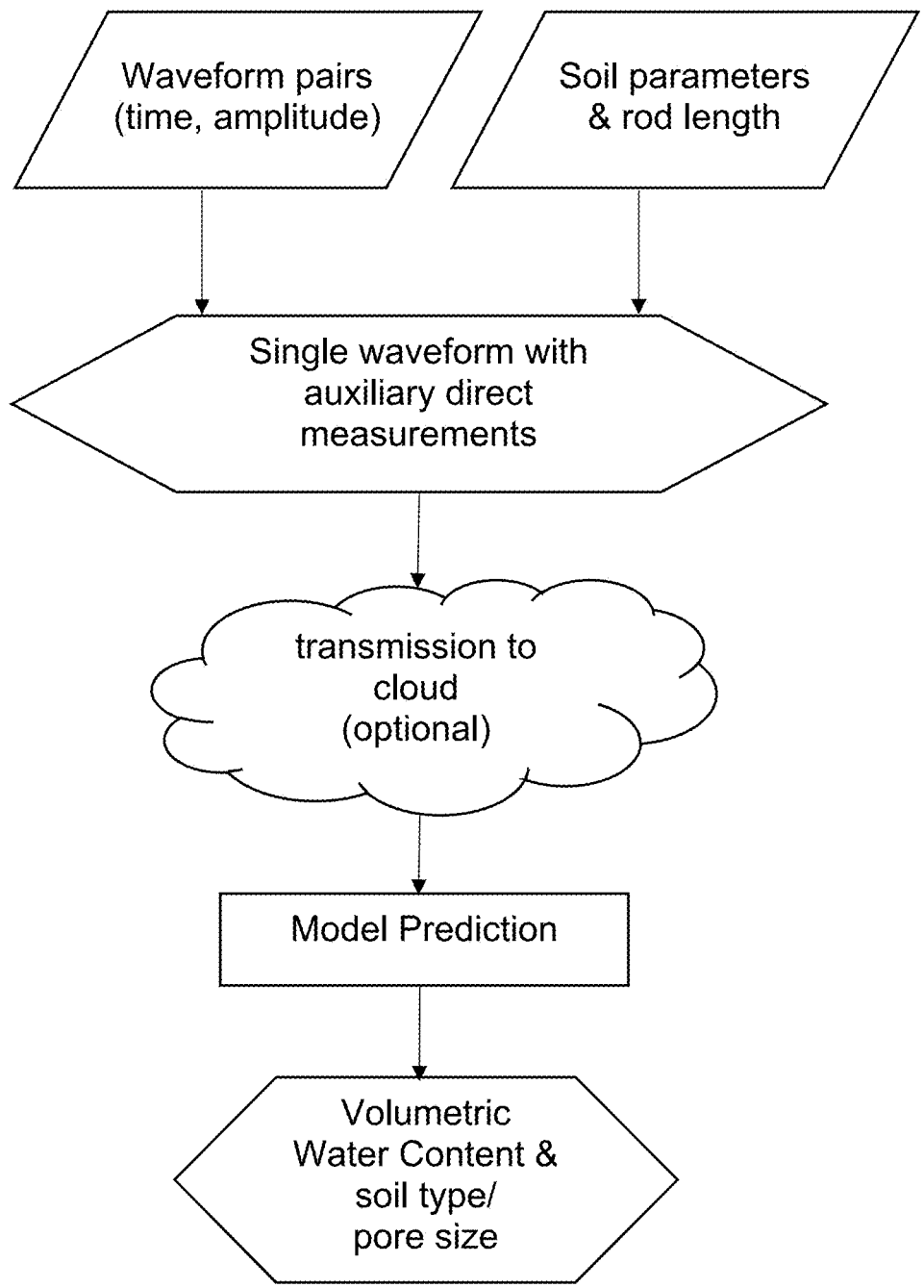
FIG. 6 is a block illustration of deployment of a Model.

Deployment of a model follows the flow of FIG. 6. Waveforms are collected and digitized to produce (time, amplitude) waveform pairs. These are matched with measurable values of soil parameters and the rod length of the waveguide. An optional transmission of this information may be made over the Internet to a cloud-based processor where a model predicts volumetric water content and soil type and/or pore size. Alternately, the transmission of information may be bypassed, implementing model prediction directly in the Time-Domain Sensor for in situ estimation of volumetric water content and soil type.

An in-cloud deployment option uses a fully integrated TDR sensor system encapsulated in a buried enclosure to acquire input data from the sensors. A waveform is captured and packaged with direct measurement data in a single compressed data file, such as a compressed msgpack or JSON file, and POSTed to a RESTful interface. This is transmitted via a radio or Internet gateway to be stored in cloud-based data storage device for use by a cloud-based computer system where the waveform analytics are executed. The cloud-server queries the pre-trained model using the input data, and responds with a characterization of soil type and pore size along with the volumetric water content. Model querying leverages common deep learning software packages such as tensorflow, CNTK, torch or theano. The results of the remote analysis are used to increase the precision of the sensor-reported water content and to derive and report soil type.

Implementing the empirical deep learning model directly within the soil moisture sensor for in situ empirical model prediction places a fully integrated TDR sensor system encapsulated in a buried enclosure. The included microprocessor with associated data storage device implements firmware algorithms derived from previous deep learning techniques applied to thousands of waveforms from soil samples of precisely known water content, soil type, electrical conductivity and temperature. This sensor uses these algorithms to report water content more accurately than would normally be reported without these additional analytics. It also uses the same analytics to derive and report soil type.

This approach imposes hard engineering restrictions on the model size and computational complexity of the model. The resultant complex soil moisture sensor must be efficient with respect to power, memory and computational capability and must be executable by a microprocessor. Thus, the model may be trained using many fewer weights than as described above for the cloud-based model. Furthermore, evaluation of the model likely requires custom programming of the microprocessor to implement microprocessor-friendly convolutions, matrix multiplies, and activation functions, as well as Analog-Digital Conversion sample caching constricted by limited memory.

The above discussion has described specific approaches to the prediction of soil types and pore sizes. It will be recognized by those skilled in these arts that variations of the described methods are possible. Though the focus here has been on data collected from Time-Domain Sensors and the use of the deep learning techniques, whether cloud-based or in situ, the referenced devices and techniques may certainly be applied in many alternative combinations to be limited only by what is described in the attached claims. Additionally, though most references to Time-Domain Sensors here have used a Time Domain Reflectometer (TDR) as an example, similar techniques may use a Time Domain Transmissometer (TDT) as well.

What is claimed is:

1. A system for estimating properties of a soil sample, the system comprising:
   a sensor having capability to acquire a digitized electromagnetic time-domain waveform when embedded in a soil specimen;
   a multitude of precharacterized soil specimen, each of which is classified by a first subset of measured soil parameters and by a second subset of physical soil parameters;
   a computing system executing a training stage configured to
      acquire the digitized electromagnetic time-domain waveform for each of the multitude of precharacterized soil specimen,
      associate the first subset of measured soil parameters and the second subset of physical soil parameters with a respective digitized electromagnetic time-domain waveform acquired from the multitude of precharacterized soil specimen,
      produce a data entry for each soil specimen, and
      collect the data entry for a multitude of soil specimen to develop a collection of data, and
      apply machine learning to predict the second subset of physical soil parameters from the collection of data, comprising the first subset of measured soil parameters and the digitized electromagnetic time-domain waveform and to produce one or more empirical soil models; and
   a post-training classifying stage configured to
      acquire the digitized electromagnetic time-domain waveform taken from the soil sample in conjunction with the first subset of measured soil parameters taken from the soil sample, and
      predict the second subset of physical soil parameters using the one or more empirical soil models, the digitized electromagnetic time-domain waveform taken from the soil sample, and the first subset of measured soil parameters taken from the soil sample, and
      report an estimate of the second subset of physical soil parameters from which the digitized electromagnetic time-domain waveform was taken.

2. The system of claim 1,
   wherein the first subset of measured soil parameters comprises one or more of temperature and electrical conductivity, and
   wherein the second subset of physical soil parameters predicted in the post-training classifying stage comprises one or more of permittivity, volumetric water content, soil type, soil particle surface area per unit volume and pore size.

3. The system of claim 1, wherein the sensor may be a waveform-digitizing Time Domain Reflectometer (TDR) or a waveform-digitizing Time Domain Transmissometer (TDT).

4. The system of claim 1, wherein a selected model is selected from the one or more empirical soil models to improve measurement accuracy of permittivity over a wide range of soil parameters.

5. The system of claim 1, wherein a selected model is selected from the one or more empirical soil models to improve measurement accuracy of volumetric water content over a wide range of soil parameters.

6. The system of claim 5, wherein the selected model accepts as input a set of measured time-domain waveform data taken from a measured soil sample and directly produces as output a value of volumetric water content of the measured soil sample.

7. The system of claim 1, wherein the one or more empirical soil models generated is for a selected soil attribute.

8. The system of claim 7, wherein the selected soil attribute is soil type.

9. The system of claim 7, wherein the selected soil attribute is one of soil pore size or soil particle surface area per unit volume.

10. The system of claim 1, further comprising
a radio transmitter in communication with the sensor enabling the sensor to transmit digitized electromagnetic time-domain waveform data and the first subset of measured soil parameters via a radio or Internet gateway to a cloud-based computing system, and
wherein the second subset of physical soil parameters predicted in the post-training classifying stage is retrieved from the cloud-based computing system.

11. The system of claim 10,
wherein the first subset of measured soil parameters comprises one or more of temperature, and electrical conductivity of the soil sample, and
wherein the second subset of physical soil parameters predicted in the post-training classifying stage comprises one or more of permittivity, volumetric water content, soil type and pore size.

12. The system of claim 1,
wherein at least one of the one or more empirical soil models is integrated as an in situ empirical model with the sensor to produce an Integrated waveform-digitizing time-domain sensor, and
wherein the Integrated waveform-digitizing time-domain sensor captures time-domain waveform data, temperature, and electrical conductivity of the soil sample as captured inputs, and
wherein applying the captured inputs to the in situ empirical model predicts as output one or more of permittivity, volumetric water content, soil type and pore size.

13. The system of claim 1, wherein the computing system configured to apply machine learning comprises a deep neural network having as inputs measurements of time and amplitude of the digitized electromagnetic time-domain waveform.

14. The system of claim 13, wherein the deep neural network comprises:
one or more convolutional layers; and
one or more fully-connected hidden layers.

15. The system of claim 14, wherein soil and sensor parameters are applied to the one or more fully-connected hidden layers.

* * * * *